United States Patent
Blom et al.

(10) Patent No.: US 7,025,784 B1
(45) Date of Patent: Apr. 11, 2006

(54) METHOD AND APPARATUS FOR A TRACHEAL VALVE

(75) Inventors: Eric D. Blom, Indianapolis, IN (US); Mark I. Singer, Indianapolis, IN (US)

(73) Assignee: Hansa Medical Products, Inc., Indianapolis, IN (US)

( * ) Notice: Subject to any disclaimer, the term of this patent is extended or adjusted under 35 U.S.C. 154(b) by 0 days.

(21) Appl. No.: 06/316,055

(22) Filed: Oct. 29, 1981

(51) Int. Cl.
*A61F 2/20* (2006.01)
(52) U.S. Cl. .................. 623/9; 623/14.11; 623/23.68
(58) Field of Classification Search ........... 128/207.14, 128/207.15, 207.16, 207.17; 3/1.3; 623/9, 623/14.11, 23.68; 137/513.3, 851, 854, 855; 251/336, 207

See application file for complete search history.

(56) References Cited

U.S. PATENT DOCUMENTS

| | | | | |
|---|---|---|---|---|
| 1,835,757 A | * | 12/1931 | Burchett | 128/207.17 |
| 3,137,299 A | * | 6/1964 | Tabor | 3/1.3 X |
| 3,262,447 A | * | 7/1966 | Burke | 128/207.16 |
| 3,330,271 A | * | 7/1967 | Hozier | 128/207.14 X |
| 3,633,605 A | * | 1/1972 | Smith | 137/512.15 X |
| 3,747,127 A | | 7/1973 | Taub | |
| 3,920,009 A | * | 11/1975 | Olsen | 128/201.13 |
| 3,924,637 A | * | 12/1975 | Swanson | 128/207.16 |
| 3,952,335 A | * | 4/1976 | Sorce et al. | 128/207.16 X |
| 4,044,402 A | * | 8/1977 | Edwards | 3/1.3 |
| 4,325,366 A | * | 4/1982 | Tabor | 128/207.16 |
| 4,808,183 A | * | 2/1989 | Panje | 623/9 |

OTHER PUBLICATIONS

Drs. Mark I. Singer and Eric D. Blom, *An Endoscopic Technique for Restoration of Voice after Laryngectomy*, Annals of Otology, Rhinology, and Laryngology, Nov.-Dec., 1980.
Dr. Stanley Taub, *Air Bypass Voice Prosthesis for Vocal Rehabilitation of Laryngectomies*, Annals of Otology, Rhinology and Laryngology, Jan.-Feb., 1975.
Drs. Stanley Taub and Lloyd Bergner, *Air Bypass Voice Prosthesis for Vocal Rehabilitation of Laryengectomies*, The American Journal of Surgery, Jun., 1973.
Drs. Shedd, et al., *Reed-Fistula Method of Speech Rehabilitation after Laryengectomy*, The American Journal of Surgery, vol. 124, 1972.
J. N. Graham, *A Layngeal Prosthesis for Fistula Speech After Laryngectomy*, Journal of Medical Engineering and Technology, vol. 1, No. 4 (Jul. 1977).

(Continued)

*Primary Examiner*—Corrine McDermott
*Assistant Examiner*—Thomas J. Sweet
(74) *Attorney, Agent, or Firm*—Barnes & Thornburg LLP

(57) ABSTRACT

An externally worn tracheal valve has a valve assembly supporting a flexible, resilient lightweight diaphragm centrally thereof. The diaphragm is folded towards the trachea so that air expelled from the trachea will tend to unfold the diaphragm to an extended position to close the valve. During normal breathing the diaphragm remains at least partially folded and the valve remains open. During voice exhalation, the diaphragm extends to close the valve. During high pressure coughing exhalation, the diaphragm may evert, opening the valve to release excessive pressure.

36 Claims, 2 Drawing Sheets

OTHER PUBLICATIONS

The Montgomery Silicone Tracheal Canula and Respiratory Valve, Massachusetts Eye and Ear Infirmary, 243 Charles Street, Boston, Mass. 02114.

Sisson, McConnel, Logemann, & Yeah, Jr., *Voice Rehabilitation After Laryngectomy, Arch Otolaryngol* vol. 101, Mar. 1975.

* cited by examiner

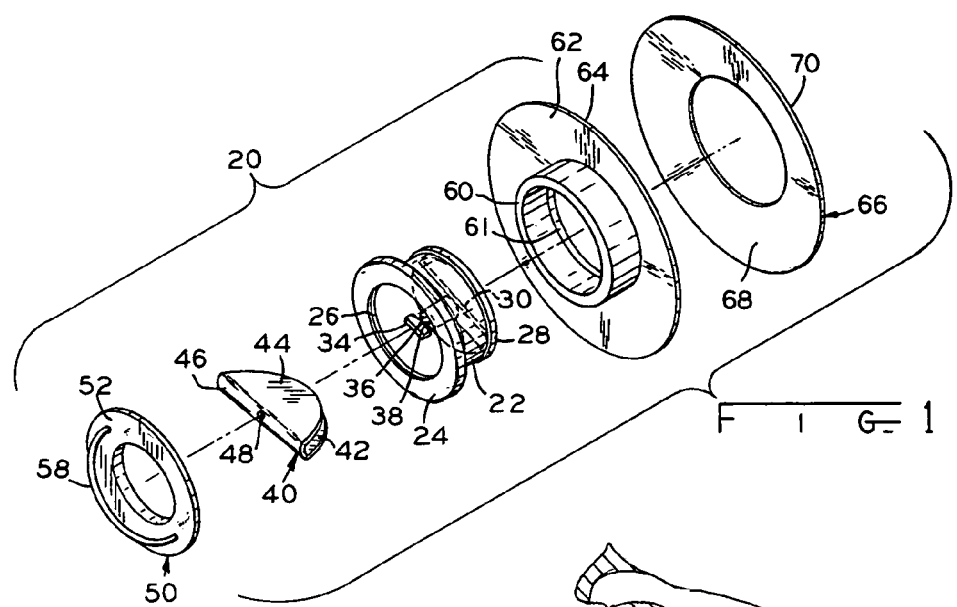
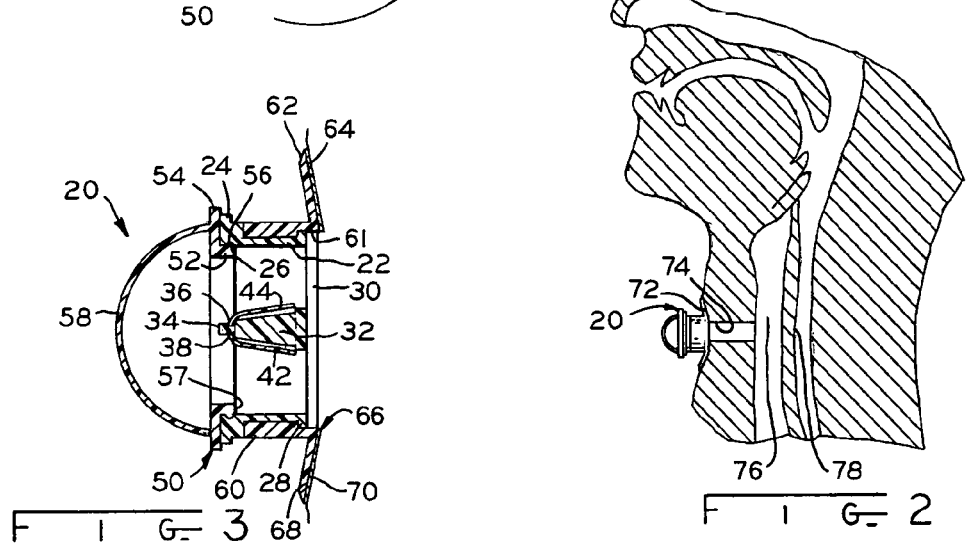
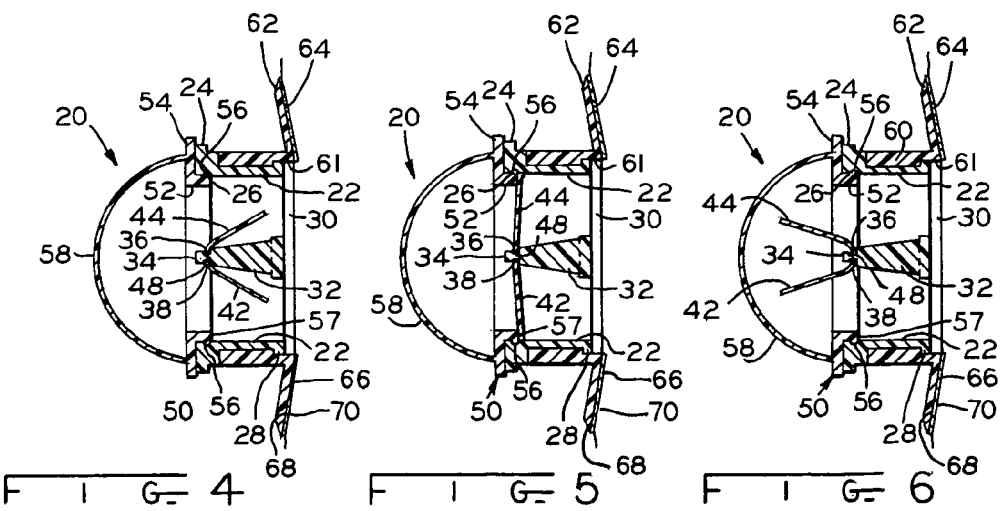

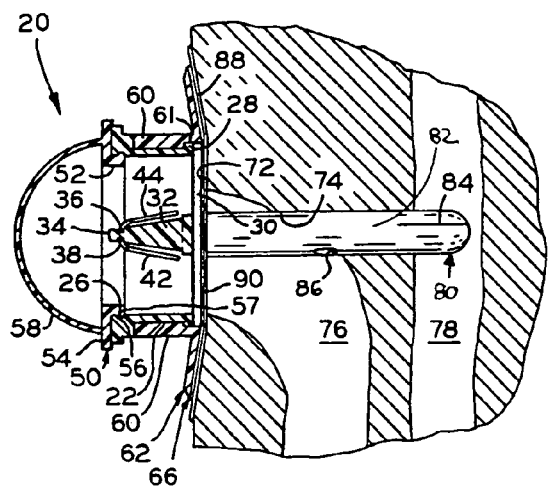
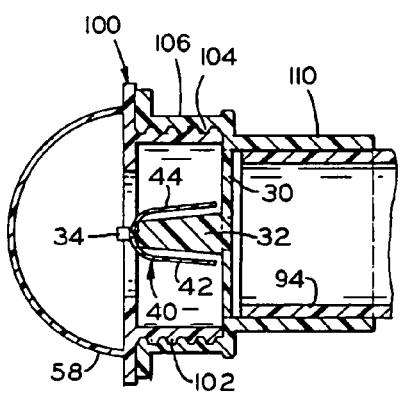
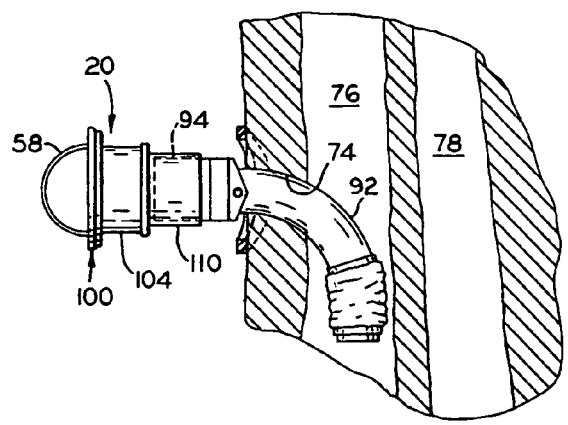

METHOD AND APPARATUS FOR A TRACHEAL VALVE

BACKGROUND OF THE INVENTION

This invention is in the field of tracheal valves used after a tracheotomy for breathing and in conjunction with a voice prosthesis device.

Numerous efforts have been made at providing a tracheal valve that will remain open to accommodate normal breathing, will close during speaking so that the voice exhalation will be diverted to the larynx or a voice prosthesis device, and will open upon coughing to relieve excessive internal pressure. Since normal breathing, voice exhalation, and cough exhalation are accompanied by progressively increasing pneumatic tracheal pressure and flow, demands are placed on the valve that are not fully met by prior valves which either are unable to or require manual adjustment to meet the demands. Further, prior valves have internal rather than external tracheal attachments that are awkward to use and/or require neck band supports, are frequently bulky and unattractive and are relatively complex in construction.

It is therefore desirable to provide a tracheal valve that will automatically remain open during normal breathing, will close during voice exhalation and will open during coughing, and is simple in construction, relatively small in size, reliable in operation, convenient and durable in use and affixed over rather than in the tracheal air way.

SUMMARY OF THE INVENTION

Therefore it is a primary object of this invention to provide an improved tracheal valve that is versatile in operation, reliable, convenient and durable in use, and simple in construction.

It is another object to provide an improved tracheal valve that will automatically adjust to the various breathing, voice, and coughing conditions.

A further object is to provide an improved tracheal valve that is relatively small in size and can be hidden by clothing in use.

Another object is to provide an improved tracheal valve that can be varied to suit the user's breathing condition.

Another object of this invention is to provide an improved tracheal valve having a convenient and reliable attachment over rather than in the tracheo-stoma.

A further object of this invention is to provide an improved tracheal valve that is adaptable for use with a voice prosthesis and/or existing tracheotomy tubes.

It is another object of this invention to provide an improved tracheal valve meeting all of the above identified objects.

In the broader aspects of this invention, there is provided an improved externally worn tracheal valve having a flexible resilient lightweight circular diaphragm that has a diametral fold and is centrally supported in a collar shaped valve body. The fold opening is towards the trachea and is opened by exhalation from the trachea. The diaphragm thickness is such that during normal breathing the diaphragm remains in a fold configuration but on voice exhalation it unfolds and occludes the valve opening to divert voice exhalation to the larynx or a voice prosthesis. During a high pressure cough, the diaphragm may evert and thus provides a valve opening.

The valve assembly has an adhesive coated resilient annular skirt that makes an acute angle with the valve axis and adheringly seats on an adhesive concave washer which is adhesively attached to the tissue around the stoma. The valve may be used with or without a voice prosthesis. The diaphragm is interchangeable with a different thickness diaphragm to suit the user's pulmonary status.

BRIEF DESCRIPTION OF THE DRAWINGS

The above mentioned and other features and objects of this invention and the manner of obtaining them will become more apparent and the invention itself will be best understood by reference to the following description of an embodiment of the invention taken in conjunction with the accompanying drawings, wherein:

FIG. 1 is an exploded perspective view of the improved tracheal valve of this invention;

FIG. 2 is a partial sectioned view of the improved tracheal valve of this invention circumferentially affixed to the skin arround the tracheo-stoma;

FIG. 3 is an enlarged sectioned view of the improved tracheal valve of this invention with the diaphragm in apposition for inhalation;

FIG. 4 is a view similiar to FIG. 3 showing a diaphragm position for normal exhalation;

FIG. 5 is a view similiar to FIG. 3 showing a diaphragm position for voice exhalation;

FIG. 6 is a view similiar to FIG. 3 showing the diaphragm in an everted position for cough exhalation;

FIG. 7 is a sectioned, partial view of the improved tracheal valve of this invention used with a voice prosthesis;

FIG. 8 is a sectioned partial view of a modified tracheal valve of this invention used with a tracheotomy tube; and FIG. 9 is an enlarged, sectioned, partial view of the tracheal valve and tube of FIG. 8.

DESCRIPTION OF A SPECIFIC EMBODIMENT

Referring to FIGS. 1–6, valve assembly 20 comprises a collar shaped body 22 having annular outwardly extending flange 24 at a first end, annular groove 26 formed in its inner wall adjacent its first end, annular rib 28 on its outer wall at its second end and cross bar 30 extending diametrally across its second end, each end of bar 30 being secured to body 22. Post 32 is secured at one end to the center of bar 30 and extends axially of body 22 towards the first end. Post 32 is tapered towards its other end to which is secured a T-shaped or enlarged retainer 34 which forms opposed recesses or recess portions 36, 38 with the end of post 32.

A flexible, resilient, lightweight, circular diaphragm 40 is formed with a diametral fold and has leaves 42, 44 which are folded along fold line 46 and are resiliently displaceable from and resiliently returnable to the fold position. Opening 48 is formed centrally of diaphragm 40 and is fittable over and around retainer 34. The periphery of opening 48 snugly fits in recesses 36, 38 and thereby retains diaphragm 40 on the end of post 32.

A ring cap 50 has a central bore 52 and annular flange 54 at one end and annular boss 56 at the opposite end. Arcuate handle 58 is secured at its ends to the outer surface of flange 54. Cap 50 is removably retained in body 22 by forceful insertion until boss 56 finds groove 26, at which point flange 54 seats snugly on flange 24 and boss 56 is positioned in groove 26. A shoulder or valve seat 57 is defined by the end of cap 50 adjacent boss 56 when inserted into body 22. Handle 58 provides a grip for removal out of sleeve 60 and also acts as a clothing guard to keep user garments and the like from interfering with valve operation or entering the stoma during use.

A flexible, resilient, cylindrical sleeve 60 has an annular recess 61 on its inside wall at one end thereof. Annular, flexible, resilient skirt 62 is secured to the outside wall of sleeve 60 opposite recess 61. The surface of skirt 62 is angled toward the wall of sleeve 60 to provide the second end of assembly 20 with a convex configuration conforming to the tissue around the stoma. A dual sided annular tape 66 is substantially coextensive with and conforming to skirt 62 and has adhesive applied to both surfaces 68, 70 thereof. Surface 64 is adhesively applied to surface 68 and surface 70 is adhesively placed on the tissue surrounding the stoma which has been surgically conformed with a concave opening and prepared to receive tape 66. Body 22 is inserted into sleeve 60 until rib 28 fits into recess 61 at which time the rim of sleeve 60 seats against the underside of flange 24 and skirt 62 is removably secured to body 22.

Referring to FIGS. 2 and 7, valve assembly 20 is shown attached to tissue 72 surrounding a tracheo-stoma 74 which provides an opening to trachea 76. In FIG. 7 a voice prosthesis 80 is shown inserted into stoma 74 through trachea 76 into esophagus 78. When the larynx has been surgically removed a voice prosthesis may be required to bypass pulmonary air through esophogeal or pharangeal tissues to produce a laryngeal psuedo voice. However, the tracheal valve of the invention can be used as shown in FIG. 8 whenever the larynx remains intact. The prosthesis 80 shown has an elongated hollow tube 82 which may be of silicone material and: has a length of 2.2 cm to 4.3 cm and an outside diameter of 5.4 mm. A razor thin longitudinal slit 84 is formed in the wall of tube 82 portion that is in esophagus 78. A port 86, in this embodiment 3.5 mm×7.0 mm, is formed on the lower side of tube 82 portion in trachea 76. Elongated straps 88, 90 are secured to and extend radially from opposite sides of tube 82 wall at the outer end thereof. Straps 88, 90 lie against the user neck exterior to provide prosthesis retention. Tape 66 is placed over straps 88, 90, valve assembly 20 is placed against tape-66 and skin surrounding the stoma, and surface 64 adheres to surface 68.

Referring now to FIGS. 3–6, the inhalation position of diaphragm 40 is shown in FIG. 3 with leaves 42, 44 lying adjacent the tapered sides of post 32. During normal breathing, leaves 42, 44 may be partially lifted by exhalation, FIG. 4, but do not occlude the valve passageway. During a voice exhalation, FIG. 5, leaves 42, 44 are fully extended and the outer perimetral border of diaphragm 40 seats against shoulder 57 to effectively occlude air passage through assembly 20 and divert air into the larynx or, in the case of FIG. 7, into prosthesis 80. Voice exhalation would then be directed into port 86 of tube 82 to exit slit 84 into the esophagus and produce a voice sound. Slit 84 acts as a one way valve preventing entrance of matter from esophagus 78 but permitting passage of air through slit 84. High pressure coughing exhalation may cause diaphragm 40 to evert, FIG. 6, forcing the perimetral edges of diaphragm 40 past shoulder 57 and through opening 32 providing for escape of cough flow.

Thus, the valve assembly 20 automatically accommodates the breath flow and pressures associated with normal breathing, speaking and coughing. If diaphragm 40 everts during high pressure coughing it is manually reset by moving leaves 42, 44 back through opening 52. Diaphragm 40 is interchangeable with diaphragms of different thicknesses to accommodate the pulmonary status of the user. For example, for those who are light breathers, such as older persons or those who suffer from emphysema, a thinner diaphragm is used. For normal breathing persons, a medium thickness is used. For heavy breathers, a thicker diaphragm is selected.

The diaphragm material may be of an opaque latex material such as sold by American Latex, Sullivan, Ind. Body 20, sleeve 60, and skirt 62 may be of a medium grade polyvinyl chloride (PVC) plastic material. The adhesive used on double sided adhesive tape 66 and skirt 62 may be a hypoallegenic adhesive tape such as 3M 1509. The surfaces surrounding the stoma may be prepared by coating with Ace adherent liquid adhesive additive available from Becton Dickinson Consumer Products.

Referring to FIGS. 8 and 9, a modified valve of this invention is shown that is usable with a conventional tracheotomy tube 92 which is inserted into the trachea below the larynx. Tube 92 will not be described except to note that it has tubular end 94 onto which the valve of this invention can be removably secured. Cap 100 has external threads 102 but otherwise is essentially the same as cap 50. Body 104 has internal threads 106 to provide for removable retention of cap 100 in body 104, but is otherwise essentially the same as body 22. Body 104 is provided a with tubular extension 110 which receives in a fluid tight friction fit end 94 therein. Cap 100 and body 104 correspond to cap 50 and body 22, respectively, in the valve of FIGS. 1–7, with the diaphragm 40 being supported and operating in the manner previously described. As desired, cap 50 and body 22 may be provided with the threads 102, 106 or, alternatively, cap 100 and body 104 may be provided with boss 56 and groove 26 to accomplish the removable retention of the caps on the bodies. Similiarly, the body 22 may be provided with an extension 110 thereby providing an adaptive connection to conventional tracheotomy tubes as desired.

While there have been described above the principles of this invention in connection with specific embodiments, it is to be understood that this is by way of example and is not limiting of the scope of this invention.

What is claimed is:

1. Apparatus for use in a tracheotomy stoma comprising: valve means for controlling fluid communication through the stoma responsive to the tracheal fluid pressure and flow; attaching means for removably attaching said valve means for fluid communication with said stoma; said valve means comprising a collar shaped cylindrical body including means for supporting a flexible, resilient diaphragm at the center of said diaphragm within said cylindrical body; the diaphragm changing in position in response to tracheal pressure and flow; said diaphragm having a first position during normal breathing to provide fluid flow through said valve means; said diaphragm being moved to a second position by voice pressure exhalation to occlude fluid flow through said valve means; said diaphragm being moved to a third position by high tracheal cough pressures to provide fluid flow through said valve means and a voice prosthesis in fluid communication with said valve means for providing voice sounds when said first means is in said second position but not in said first and third positions, said voice prosthesis extending through said tracheotomy stoma and into the esophagus of a patient.

2. The apparatus of claim 1 wherein said diaphragm comprises two leaves folded toward one another about a fold line, said leaves being resiliently displaceable from, and returnable to, the fold position; said leaves being in a folded position in the first position of said diaphragm; said leaves in an unfolded position in the second position of said diaphragm; and said leaves being in an everted position in the third position of said diaphragm.

3. The apparatus of claim 2 wherein said second means is for removably supporting said diaphragm in said body whereby said diaphragm is interchangeable with other diaphragms of different physical properties to accommodate different breathing conditions.

4. The apparatus of claim 3 wherein diaphragms of varying thicknesses are used for conditions of varying pulmonary status.

5. Apparatus for use in a tracheotomy stoma comprising: a collar shaped body having first and second axial ends; an annular shoulder being on the inner body wall at said first axial end; a flexible, resilient, circular diaphragm having leaves forming a fold, said leaves being resiliently displaceable to an unfolded position and resiliently returnable to reform said fold; attaching means for removably attaching said diaphragm to said body for valving fluid flow through said body to and from said stoma; whereby fluid may flow through said body from said stoma, said flow being into said fold causing said diaphragm to unfold, and when the flow causes the perimetral edges of said diaphragm to seat on said shoulder, said flow will be effectively occluded, and coughing pressure on said seated diaphragm will cause said diaphragm to evert, reestablishing fluid flow through said body, a ring cap frictionally held in said first end and a rim of an inserted end of said cap forming said shoulder.

6. The apparatus of claim 5 wherein said cap is snap fitted into said first end.

7. The apparatus of claim 5 wherein said cap is threaded into said first end.

8. The apparatus of claim 5 wherein said cap has an arcuate handle secured at each end to opposite perimetral points on said cap.

9. Apparatus for use in a tracheotomy stoma comprising: a collar shaped body having first and second axial ends; an annular shoulder being on the inner body wall at said first axial end; a flexible, resilient, circular diaphragm having leaves forming a fold, said leaves being resiliently displaceable to an unfolded position and resiliently returnable to reform said fold; attaching means for removably attaching said diaphragm to said body for valving fluid flow through said body to and from said stoma; whereby fluid may flow through said body from said stoma, said flow being into said fold causing said diaphragm to unfold, and when the flow causes the perimetral edges of said diaphragm to seat on said shoulder, said flow will be effectively occluded, and coughing pressure on said seated diaphragm will cause said diaphragm to evert reestablishing fluid flow through said body, a voice prosthesis adapted for insertion in the tracheal stoma; said body second end being placed over said voice prosthesis and adapted for attachment to the tissue around the stoma; whereby when said diaphragm is in said unfolded flow occluding position tracheal air flow will be directed through said voice prosthesis to produce voice sounds.

10. The apparatus of claim 9 wherein said voice prosthesis comprises an elongated tube adapted to be inserted through the trachea and into the esophagus; a longitudinal razor slit being formed in the tube portion in the esophagus to provide a one way valve; a port being formed in said tube in the trachea portion of the tube to receive tracheal air, said tube conducting said air to said slit when said diaphragm is in said unfolded flow occluding position.

11. A method for controlling fluid flow through a valve member in a tracheotomy stoma comprising changing the position of the valve member in response to tracheal pressure among a first position during normal breathing to provide fluid flow through said stoma, a second position responsive to voice exhalation to occlude fluid flow through said stoma, and a third position responsive to high tracheal cough pressures to provide fluid flow through said stoma; said valve member comprising a flexible, resilient, diaphragm having resilient leaves forming a fold in said first position, said leaves being resiliently displaceable to an unfolded second position and resiliently returnable to said first position, said leaves being resiliently moved into said third position by high tracheal cough pressures, and forcing fluid through a voice prosthesis mounted to provide fluid communication between the trachea and esophagus of the wearer by forcing said valve member into said second position, the fluid being forced from the trachea through the voice prosthesis and into the esophagus of a patient.

12. Apparatus for use in a tracheotomy stoma comprising valve means for controlling communication through the stoma responsive to the tracheal air pressure; attaching means for removably attaching said valve means for communication with said stoma; a voice prosthesis, means for coupling the voice prosthesis to the valve means wherein the voice prosthesis extends through the tracheotomy stoma and into the esophagus of a patient; said valve means having first means for changing in position in response to tracheal pressure; said first means having a first position during normal breathing to provide air flow through said valve means; said first means being moved to a second position by voice pressure exhalation to occlude air flow through said valve means, forcing air through said voice prosthesis; said first means being moved to a third position by high tracheal cough pressures to provide air flow through said valve means.

13. The apparatus of claim 12 wherein said valve means comprises a body having first and second axial ends; said second end having a resilient, flexible, annular skirt flared away from said body to provide a surface configured to conform to the tissue around said stoma; the attaching means removably attaching said skirt to the tissue around said stoma.

14. The apparatus of claim 12 wherein said attaching means comprises tape having adhesive on both sides; said tape attaching said skirt to the tissue of the patient's neck around said stoma.

15. The apparatus of claim 12 wherein said valve means comprises a cylindrical body having a second means for supporting a flexible, resilient diaphragm, said first means comprising said diaphragm.

16. The apparatus of claim 15 wherein said diaphragm comprises two leaves folded toward one another about a fold line, said leaves being resiliently displaceable from, and returnable to, the folded position; said leaves being in a folded position in the first position of said diaphragm; said leaves in an unfolded position in the second position of said diaphragm; and said leaves being in an everted position in the third position of said diaphragm.

17. The apparatus of claim 15 wherein said second means further includes means for removably supporting said diaphragm in said body and further comprising additional diaphragms said diaphragm being interchangeable with said additional diaphragms of different physical properties to accommodate different breathing conditions.

18. The apparatus of claim 17 wherein said additional diaphragms having different physical properties comprise diaphragms having different thicknesses.

19. The apparatus of claim 18 wherein said attaching means comprises tape for attaching said skirt to the tissue of the patient's neck around said stoma.

20. A valve for use with a tracheotomy stoma comprising: a valve body having an air passageway therethrough, said valve body including means for connecting said passageway with a tracheotomy stoma, a post in said air passageway, means for centering said post in said air passageway and allowing passage of air through said air passageway, a flexible diaphragm whose center is attached to said post and sized to fit within said air passageway, and a valve seat comprising an annular shoulder at one end of said air passageway and spaced a predetermined distance from said diaphragm, said valve seat having an opening therethrough smaller than said diaphragm, said flexible diaphragm being so constructed that it allows air to flow around its periphery through said air passageway in either direction when air velocity is at a rate present while breathing normally through said tracheotomy stoma and moves into sealing engagement with said valve seat when air is exhaled through said tracheotomy stoma at a rate above that present when breathing normally thereby blocking said air passageway, and means for adjusting the distance between said valve seat and said flexible diaphragm for adjusting the rate of air flow around said flexible diaphragm before said air passageway is blocked.

21. A valve according to claim 20 wherein said valve body has a first barrel and said flexible diaphragm means is centered at one end thereof, said valve seat has a second barrel with an annular shoulder in one end, the other end of said second barrel sized to be inserted into said first barrel around the periphery of said flexible diaphragm means, and said adjusting means comprises helical threads between said first and second barrels for allowing said second barrel to be screwed a variable distance into said first barrel for varying the distance between said annular shoulder and said flexible diaphragm means.

22. A valve according to claim 21 wherein said centering means is a plurality of arms forming a spider at the end of said first barrel opposite said flexible diaphragm means, and said center post is connected at one end to the center of said spider and extends to said flexible diaphragm means on the central longitudinal axis of said first barrel.

23. A valve according to claim 22 wherein said second barrel has means for facilitating manual rotation of said second barrel within said first barrel.

24. A method of blocking air flow through a tracheotomy stoma responsive to a predetermined elevated pressure in said tracheotomy stoma comprising centering a flexible diaphragm in a flow passageway connected to said tracheotomy stoma that is constructed to allow air to flow around its periphery through said flow passageway in either direction when the air velocity is at a rate present while breathing normally through said tracheotomy stoma and moves into sealing engagement with said valve seat when air is exhaled through said tracheotomy stoma at a rate above that present when breathing normally thereby blocking said air passageway, adjustably locating a valve seat a predetermined distance from said flexible diaphragm, allowing air flow through an opening in said valve seat and around the periphery of said flexible diaphragm in either direction when the rate of flow of air through the tracheotomy stoma is that present while breathing normally, and moving said flexible diaphragm into sealing engagement with said valve seat for blocking the flow of air out of said tracheotomy stoma responsive to pressure in said tracheotomy stoma greater than that present while breathing normally.

25. A valve for use with a tracheotomy stoma, comprising a base having a tubular portion and an outwardly directed flanged portion, said flanged portion made of flexible material for sealing engagement with the paratracheal skin around the stoma of a patient, a valve body inserted into the tubular portion of said base, said valve body comprising a first barrel having a first end sized for insertion into the tubular portion of said base, a plurality of arms in said first barrel forming a spider in said barrel, a post attached at one end to the center of said spider and extending along the central longitudinal axis of said first barrel to the second end of said first barrel, flexible diaphragm means attached to said post and centered in said first barrel at right angles to said post, a second barrel having a first end slidably inserted into said first barrel, said second barrel having an inner diameter slightly larger than the diameter of said diaphragm means thereby defining an annular space around the periphery of said flexible diaphragm means, helical threads between said first and second barrels wherein said second barrel is operable to be screwed a variable distance into said first barrel, said second barrel having an inwardly directed shoulder at the second end for providing a valve seat for said flexible diaphragm means, said flexible diaphragm means being so constructed that it allows air to flow around its periphery through said second barrel in either direction when the air velocity is at a rate present while breathing normally through said tracheotomy stoma and moves into sealing engagement with said valve seat when air is exhaled through said tracheotomy stoma at a rate above that present when breathing normally thereby blocking air flow through said second barrel, the distance between said diaphragm means and said valve seat being adjustable by rotation of said second barrel within said first barrel, and an outwardly directed flange on the second end of said second barrel extending outwardly past the sides of said first barrel for facilitating the manual rotation of said second barrel within said first barrel.

26. A valve for use with a tracheotomy stoma comprising a first barrel having a passageway therethrough and a post in said passageway, said first barrel including means for connecting said passageway with a tracheotomy stoma, means for centering said post in said passageway, a flexible circular diaphragm located at one end of said first barrel whose center is attached to said post, and a second barrel having one end slidably inserted in said first barrel and having an air passageway therethrough and an annular shoulder at the other end which annular shoulder projects radially inward towards the center of said air passageway and defines a valve seat for said diaphragm having an opening smaller than the surface of said flexible diaphragm, said flexible diaphragm being so constructed that it allows air to flow around its periphery through said second barrel in either direction when the air velocity is at a rate present while breathing normally through said tracheotomy stoma and moves into sealing engagement with said valve seat when air is exhaled through said tracheotomy stoma at a rate above that present when breathing normally thereby blocking air flow through said second barrel, said second barrel having an inner diameter slightly larger than the diameter of said diaphragm thereby defining an annular space around the periphery of said flexible diaphragm and means for adjusting the distance between said annular shoulder and said flexible diaphragm for adjusting the rate of air flow around said flexible diaphragm before said air passageway is blocked.

27. A valve according to claim 26 wherein said adjusting means comprises helical threads between said first and said second barrels for allowing said second barrel to be screwed a variable distance into said first barrel for varying the distance between said annular shoulder and said flexible diaphragm.

28. A valve according to claim 27 wherein said centering means is a plurality of arms forming a spider at the end of said first barrel opposite said flexible diaphragm, and said center post is connected at one end to the center of said spider and extends to said flexible diaphragm on the central longitudinal axis of said first barrel.

29. A valve according to claim 28 wherein said second barrel has means for facilitating manual rotation of said second barrel within said first barrel.

30. A method of producing alaryngeal pseudo voice comprising the steps of placing a valve means in sealing engagement about a tracheostomy stoma in the neck of a patient; coupling a voice prosthesis to the valve means wherein the voice prosthesis extends through the tracheotomy stoma, through the esophageal tissue, and into the esophagus of the patient; changing the position of a valve member within the valve means in response to tracheal pressure; the positions comprising a first position during normal breathing to provide air flow through the stoma and valve means; a second position responsive to higher tracheal pressures to occlude the air flow through the stoma and the valve means, the occlusion forcing air through the voice prosthesis into the esophagus; and a third position responsive to high tracheal cough pressure to provide air flow through said stoma.

31. Apparatus for use in a tracheotomy stoma comprising a valve for controlling communication through the stoma responsive to the tracheal air pressure; a voice prosthesis providing an airway between the trachea and the esophagus of a patient; adhesive for removably attaching the valve for communication with the stoma; the valve having a first position during normal breathing to provide air flow through the valve; the valve being moved to a second position by voice pressure exhalation to occlude air flow through the valve, preventing air flow through the stoma, the air being diverted through the voice prosthesis into the esophagus of the patient, the valve comprising a body having a resilient, flexible, annular skirt flared away from the body to provide a surface configured to conform to the tissue around the stoma; the adhesive provided on the skirt for removably attaching the skirt to the tissue around the stoma.

32. The apparatus of claim 31 wherein the adhesive comprises tape having the adhesive thereon; the tape attaching the skirt to the tissue of the patient's neck around the stoma.

33. Apparatus for use in a tracheotomy stoma comprising a valve for controlling communication through the stoma; a voice prosthesis providing an airway between the trachea and the esophagus of a patient; adhesive for removably attaching the valve for communication with the stoma; the valve having a first position to provide air flow through the valve; the valve being moved to a second position to occlude air flow through the valve, preventing air flow through the stoma, the air being diverted through the voice prosthesis into the esophagus of the patient, the valve comprising a body having a resilient, flexible, annular skirt flared away from the body to provide a surface configured to conform to the tissue around the stoma; the adhesive provided on the skirt for removably attaching the skirt to the tissue around the stoma.

34. The apparatus of claim 33 wherein the adhesive comprises tape having the adhesive thereon; the tape attaching the skirt to the tissue of the patient's neck around the stoma.

35. A device for placement over a tracheostoma of a wearer, the device including a cylindrical sleeve, an annular flexible resilient skirt projecting outward from an outside wall of the sleeve for attachment to the skin of the wearer around the tracheostoma, a body including a passageway for communicating with the tracheostoma, one of the cylindrical sleeve and the body including an annular recess on a side wall thereof and the other of the cylindrical sleeve and the body including an annular outwardly extending rib, the body and the sleeve being pushed into engagement until the rib engages the recess, removably securing the skirt to the body.

36. The device of claim 35 including adhesive on a side of the annular flexible resilient skirt for attaching the annular flexible resilient skirt to the skin of the wearer around the tracheostoma.

\* \* \* \* \*